US010012607B2

(12) United States Patent
Pleten

(10) Patent No.: US 10,012,607 B2
(45) Date of Patent: Jul. 3, 2018

(54) DETERMINATION OF THE REMOTENESS OF AN EVENT OF A MAN MADE OBJECT CREATION FOR PROTECTION AGAINST FALSIFICATION

(76) Inventor: Oleg Ivanovich Pleten, Krasnodar (RU)

( * ) Notice: Subject to any disclaimer, the term of this patent is extended or adjusted under 35 U.S.C. 154(b) by 131 days.

(21) Appl. No.: 14/366,304

(22) PCT Filed: Dec. 19, 2011

(86) PCT No.: PCT/RU2011/001001
§ 371 (c)(1),
(2), (4) Date: Nov. 18, 2014

(87) PCT Pub. No.: WO2013/095172
PCT Pub. Date: Jun. 27, 2013

(65) Prior Publication Data
US 2015/0064427 A1   Mar. 5, 2015

(51) Int. Cl.
*G01N 24/08* (2006.01)
*G01R 33/44* (2006.01)

(52) U.S. Cl.
CPC .......... *G01N 24/08* (2013.01); *G01R 33/448* (2013.01); *Y10T 428/24934* (2015.01)

(58) Field of Classification Search
CPC . G06K 19/02; G06K 7/00; G09F 3/00; G01N 24/08; G01R 33/448; Y10T 428/24934

(Continued)

(56) References Cited

U.S. PATENT DOCUMENTS 3,638,340 A  *  2/1972  Gottschalk ............ G09F 3/0288
                                                   283/103
6,397,334 B1 *  5/2002  Chainer .................. G01S 17/88
                                                   380/200
(Continued)

FOREIGN PATENT DOCUMENTS

DE          3603599 A1      8/1987
EP          1569166 A2      8/2005
(Continued)

OTHER PUBLICATIONS

International Search Report for PCT/RU2011/001001, completed Aug. 6, 2012, 3pp. and English translation, 1p.

*Primary Examiner* — Randy Gibson
*Assistant Examiner* — Gedeon M Kidanu
(74) *Attorney, Agent, or Firm* — Locke Lord LLP

(57) ABSTRACT

A method is provided to determine a remoteness of an event of creation of a man-made object made of a cellulose-containing material or a man-made object having on its surface fragments made of a cellulose-containing material and having surface areas with no coating and areas with a coating by means of measured and calculated relative changes of the cellulose parameters in surface layer of the cellulose-containing material at some pair of said surface areas with no coating and under the coating at the moment of study starting and at the moment after a predetermined time interval sufficient for any changes of said cellulose parameters being taken place and calculate the remoteness of an event of creation of a man-made object or its surface fragments according to the time point when there were no said relative changes.

22 Claims, 3 Drawing Sheets

(58) Field of Classification Search
USPC .... 235/435, 462.01, 468, 469, 487; 427/7, 8
See application file for complete search history.

(56) References Cited

U.S. PATENT DOCUMENTS

| | | | | |
|---|---|---|---|---|
| 7,865,722 | B2* | 1/2011 | Moran | G06K 19/06196 |
| | | | | 713/161 |
| 8,439,258 | B1* | 5/2013 | Hood | G06K 7/00 |
| | | | | 235/435 |
| 8,931,696 | B2* | 1/2015 | Hood | G06K 7/00 |
| | | | | 235/435 |
| 2009/0103098 | A1* | 4/2009 | Lightening | G09F 3/00 |
| | | | | 356/445 |
| 2009/0220789 | A1* | 9/2009 | DeSimone | B82Y 10/00 |
| | | | | 428/402 |
| 2013/0240630 | A1* | 9/2013 | Hood | G06K 7/00 |
| | | | | 235/487 |

FOREIGN PATENT DOCUMENTS

| | | |
|---|---|---|
| RU | 2199781 C1 | 2/2003 |
| RU | 2281552 C2 | 8/2006 |
| RU | 57488 U1 | 10/2006 |

* cited by examiner

DETERMINATION OF THE REMOTENESS OF AN EVENT OF A MAN MADE OBJECT CREATION FOR PROTECTION AGAINST FALSIFICATION

FIELD OF INVENTION

The invention relates to a technical examination of the remoteness of an event of creation of various types of man-made objects made of a cellulose-containing material or the objects having on its surface a fragment of a cellulose-containing material having on its surface at least one first area exposed to the environment having no coating, and at least one coated area. The invention also relates to methods for determination of the remoteness of an event of application of a coating on said object or on said fragment.

In particular, the invention relates to a method for determination of the remoteness of an event of a man-made object creation when the man-made object is made of a cellulose-containing material having on their surface an applied image made of paper, fabric, a papier-mache, wood in the form of industrial goods, articles of individual creativity and individual use, for example, printed matter, a souvenir article, a figurine, a piece of furniture, a loomwork, a hand weaving article, a picture, various printed and hand-written documents including coated areas, made by coating the surface of a cellulose-containing material with various types of the coating materials applied by jet of another printing technique, contact technique, hand-writing or other methods: colouring agents, varnishes, mastics any art colours, printing inks, stamping inks, pastes (for example, those for ball pens), powders (for example, for cartridges of printing devices), ink (for example, for pen-type, capillary, gel and fountain pens, felt pens), biopolymeric ink for pens, and other coatings.

BACKGROUND OF THE INVENTION

In view of the wide use of cellulose which is a natural biopolymer having a complex structure and special physical and chemical properties, used for creation during the various historical periods of man activity, of objects of culture, author's right objects, individual creativity articles, various constitutive documents, archive documents of private use and other objects and articles, a very important problem in the archive, antiquarian, criminalistic and judicial activity consists in establishing the correspondence of the claimed date of creation of an article, an object or its fragment to its true (valid) creation date.

At present there are known various methods for determining the age of cellulose-containing materials wherein estimation of respective changes in the physical and chemical properties and the cellulose structure under the environmental effects are determining, said methods being used for estimating the age of the object as a whole object including an object having an image on the surface of the cellulose-containing material which can be made of other materials during the various periods of the life of the cellulose-containing carrier.

Known in the art is a method for determining the age of a carrier made of a based-cellulose material (RO, 116844) which is used for establishing the date of writing of documents, mainly, in determination of the intervention process required for recovery and saving of manuscripts, products of the early period and old books by means of sampling and determination of the level of whiteness in the initial phase and after the heat treatment at 103 . . . 2 degrees centigrade.

Known in the art is a method for determining the age of a fabric made of cellulose (RO, 121151) which is used for the purpose of determining the date of creation of a picture canvas, an article of clothing and old materials by determining the degree of polymerisation of the cellulose using an alkali solution of the Schweizer's reagent.

Known in the art is a method for determining the chemical characteristics of cellulose in samples of paper by the content of carbonyl and carboxyl groups (DE, 102007-44606, B4), wherein there is studied the content of the carbonyl groups decreasing with an increase of the sample age, and the content of the carboxyl groups increasing with an increase of the paper age because of progressive processes of oxidation of the cellulose. The parameters of whiteness and density of the cellulose and paper can be found in the same way.

Known in the art is a method for determining the age of a document written on paper, for example, a manuscript (DE, 3603599, A1), wherein small samples of paper put in a solution for some time and the dissolving can be accelerated by means of ultrasonic treatment. From 5 to 7 solutions are used one after another. The obtained solutions are then subjected to a thin-layer chromatography to determine the disappearance of colour in the solution and evaluated by mathematically finding the numerical value of the gradient of the resultant curve of the exponential function which is used as an index of the document age: a higher curvature of the function corresponds to a younger document, and the smaller one corresponds a more ancient document. However, this method does not allow one to compare the age of paper with the age of the applied colour coating that is required, for example, for determining forgeries and falsification of dates and signatures on the documents.

Known in the art is a method for determining the date of creation of old materials made of cellulose-based fabrics (MID, 3325, F1) including: determination of the degree of polymerisation of the cellulose in an old material by the viscometric method, establishing the level of decomposition of the cellulose in the ratio (%)=100 $[2/(GP)_i-2/(GP)_f]$, where $(GP)_f$ is the degree of polymerisation of the cellulose in the old material, and $(GP)_i$ – is the degree of polymerisation of the cellulose in the new cotton or new cellulose mixture: flax, hemp and/or cotton equal, accordingly, to 1800 and 3100; extrapolation of the level of decomposition of the cellulose (%) on graphics representing an age equivalent of the material depending on the level of decomposition of the cellulose using various graphics for the cotton and for said cellulose mixture.

Known in the art is a method for determining the dating of creation of handwritten texts and other written materials (RU, 2296315, C1), wherein two samples of the written material being tested are obtained. One of them is extracted by a solvent and the other sample at first is heated and is then extracted under the same conditions by the same solvent. The extraction results quantitative comparison is made, before the quantitative comparison of both samples are subjected to spectrophotometric analysis in which there is obtained a relation of the optical densities in the field of maximum of peaks of the colouring agents per unit length a dash sample of each sample calculating the ratio of the optical densities in the field from 400 to 1100 nanometers. The time dating of the studied document is determined by comparing these values with the similar parameters of this documents with a certainly known date of their creation, presented in a graphical or a tabular form.

Also are known in the art the methods for determining the age of elements of images applied onto a carrier surface wherein the age of the whole document is defined.

Known in the art is a method for determining the age of ink applied on a working surface with respect to other signatures or symbols by a change of the pH factor of the chemical compounds in the ink changing the composition in process of chemical reactions therein and corresponding to the age of the ink (U.S. Pat. No. 5,600,443, A).

Known in the art is a method for determining the age of hand-written fragments and texts made by a jet printing device, printing seals and the stamps made by stamping inks using the method of gas chromatography-mass spectrometry (Aginsky V. N. «Dating and Characterizing Writing, Stamp Pad and Jet Printer Inks by Gas Chromatography/Mass Spectrometry», International Journal of Forensic Document Examiners, Vol. 2, No. 3, July/September 1996, p. 103-116). This method is based on the dependence between the age of dash samples and the content of high-boiling organic solvents in the dash samples. The study includes the solvent extraction from the tested dash sample at first with a "weak" extragent, and then with a "strong" extragent, and determination of the solvent extraction level from the dash sample which decreases with the dash sample age. Then the accelerated (artificial) aging of the tested dash samples is performed (heating to 70° C. within 4 hours) and determination of the solvent extraction level is carried out as described above. In this method the main estimation criterion of the dash sample age is the difference in the characteristics of the solvent extraction level obtained before and after the artificial aging. The determination of the difference of the level of the solvent extraction is based on the quantitative analysis of the solvent extracted from the tested dash samples by the method of gas chromatography-mass spectrometry using the internal standard. However, the method does not takes into account the effect of the following factors: the compositions of the main components of the colorant in the studied dash samples, the character of its allocation in the compared dash samples, the completeness of the dash sample surface with extragents in the course of extraction, the nature of the "strong extragent", the error of internal standard method when determining the amount of the solvent in the dash samples. Moreover, an insignificant dash sample colorant content can be determined mainly by the "background" content of solvent due to its migration from the dash sample to the other requisites.

Known in the art is a method for determination of the remoteness of the requisites in documents by relative: content of volatile solvents in their dash samples (RU, 2399042, C1), used in technical examination of documents for determining the authenticity and age of different types of documents whose requisites were made by a paste of ball pens, ink for gel pens, a jet printing method, and stamping inks. A microscopic technique is used for determining the sort of letter material in the dash samples and the fitness of the document requisites for a further study. At least two objects of study are obtained in the form of samples for analysis, one of them comprises the dash samples of the document requisites, and the other one is a piece of paper of the document free of dash. Each sample for analysis is subjected to thermal desorptions in a continuous gas flow for a certain time and at a given temperature with formation of a mixture of a carrier gas and thermal desorption products, then thermal desorption products are separated into some substances. The results of the analysis of the samples of a dash and/or paper are obtained in the graphical form of a curve, the presence and the amount of specific solvents in the dash sample are determined by the retention time and height of the peaks on the curve, the presence of thermal desorption products in the dash samples is determined in the paper products with the same retention time, as the retention time of the solvents in the examined dash samples, by the curve. The height of an appropriate peak on the curve—the dash sample chromatogram expressed in standard units taking into account the contribution of thermal desorption products from the paper being tested—is taken for the characteristic of the content of solvent in the dash sample. Then the colorant is extracted from the dash samples and the extracts obtained are subjected to a spectrophotometric analysis in the visible range of spectrum for determining the colouring agent content in the sample in the form of the obtained extract absorption spectrum curve in a spectrophotometer. However, in said method the sample of paper is used for exclusion effect of the paper thermal desorption products on the result of study of the solvents in the dash sample thermal desorption products, and this method is technologically very complicated, because it requires a significant amount of the reference data concerning the compounds consisted in a paper and a significant amount of the dash material in initial state and in the process of their age changing.

However, determination of the remoteness of an event of creation of documents as a whole man-made object by the dash age change applied thereon is not authentic since in the same document the dashes can be applied at various times in different fields of the document, for example, in case of local forgery. Besides, the study of the dash material compositions is a challenge because the change of the composition of these materials depends mainly on the conditions of plotting the dash on the document and on the conditions of subsequent state of the documents: temperature conditions of the document storage, radiation effects, steam effect and other factors.

As it is well known to specialists in the field of technical examination, at the present time the most informative parameters of the change of cellulose properties are:
 a degree of crystallinity of the cellulose;
 an average density of the amorphous regions;
 a density of distribution of protons (amount of protons) in the studied sample with respect to which various methods of their determination are developed.

It is also known that cellulose is a natural biopolymer consisting of crystalline and amorphous regions. In the course of physical and chemical effects, the volume and amount of the crystalline regions decrease and, as a consequence, the volume and amount of the amorphous regions increases that effects on the cellulose crystallinity degree and the cellulose molecular structure state characterized by the presence and density of proton distribution.

Thus, from the study of the cellulose structure by means of impulse NRM spectroscopy there is obtained a multistage NMR-relaxational function consisting of two components: a short high-relaxation component and long slow-relaxation component. It is well known that the cellulose structural characteristics are determined mainly by the short component of the relaxational function which carries information on the volume-mass ratio of the crystalline and amorphous phases of the polymer that allows one to determine not only the crystallinity degree but also to evaluate the average size of the crystalline and amorphous regions and their volumetric density.

It is also known that spin-spin relaxation time sensitively reacts to changes in the molecular system in the elementary links of the cellulose molecule: this amplitude of free induction signals (from here on referred to as the FIS) and the values of time of the spin-spin and spin-lattice relaxation allow one to obtain information on the state and properties of the cellulose when making the cellulose-containing material and when creating a man-made object having the cellulose-containing material and on their change as a result of various physical and chemical effects during the life of the cellulose-containing material.

Known in the art is a method for determining the degree crystallinity of cellulose (SU 1749800), in which a tested sample is wetted at a certain air humidity during certain time, excited and registered, for example, by means of nuclear-magnetic resonance spectroscopy, signals of the free induction (FIS) protons of the tested sample and the water reference, determine the amplitude of the standard signal $A_s$ and the amplitude of the slowly relaxing component $A_{OD}$ of the sample signal, and the degree of crystallinity is determined from the relation $$K = \frac{\frac{m_o \cdot A_\ni}{m_\ni \cdot A_{OD}} - 1}{\frac{m_o \cdot A_\ni}{m_\ni \cdot A_{OD}} - 1 + \rho_K},$$

where $m_O$ is the sample mass, g; $m^\ni$ is the mass of an aqueous standard, g; $\rho_K$ is the density in crystalline regions of the cellulose sample, g/cm$^3$.

Known in the art is a method for determining the degree of crystallinity of natural polymers (RU 2175765, C1) including excitation and recording of the characteristic signal of the tested sample, in which the tested samples are wetted from 0 to hygroscopicity with a humidity from theoretically dry state to the hygroscopic state, and the characteristic signal is registered by means of the impulse nuclear-magnetic resonance spectrometer (NMR H$^1$) of the free induction signal (FIS) of the drop of protons, then the FIS signal is used for determining the times of the spin-spin relaxation $T_{2k}$ of the short component, the humidity dependencies $T_{2k}$ are used for determining the characteristic times $T_{20}$, $T_{21}$, $T_{22}$, $T_{23}$ and the degree of crystallinity K by the formula:

$$K = 1 - \frac{(T_{21} - T_{20}) + (T_{23} - T_{22})}{T_{20}},$$

where $T_{20}$ is the time of the spin-spin relaxation of the short component of theoretically dry sample;

$T_{21}$ is the time of the spin-spin relaxation of the short component at the end of adsorption of the water molecules directly on the active centres in the amorphous regions of the polymer sample:

$T_{22}$ is the time of spin-spin relaxation of the short component at filling the monomolecular layer of the water molecules;

$T_{23}$ is the time of the spin-spin relaxation of the short component at a hygroscopic water content of the sample.

Known in the art is a method for determining proton-containing substances in the initial, intermediate and finished cellulose-based products (RU, 2053503, C1), in which the free induction signal (FIS) of protons is registered as a characteristic signal, the tested and reference samples of same mass are placed one after another in a sensor for establishing the nuclear magnetic resonance, the samples are attacked by impulses, the amplitude of the short FIS component is recorded from the initial and processed samples.

After that there are determined the amplitudes $A^{IK}$ and $A^{EK}$ of the short components of the signals, accordingly, for the tested and reference samples, and the crystallinity degree K is calculated using the formula:

$$K = 1 - (A_{И\,K} \cdot m^\ni / A^\ni{}_K \cdot m_И),$$

where $A^H$ and $A^\ni$ are the amplitudes of the short component FIS of the tested and reference samples. respectively; $m^\ni$ and $m_И$ are respectively the masses of the reference and tested samples which beforehand were dried up to a constant mass.

However the estimation of the cellulose age by one parameter only is not completely justified because in one sample of an object or an article the areas of a cellulose-containing material of various compositions can be available, in a different degree of the environmental effect, for example, in connection with the presence thereon of protecting coatings, for example, color agents, ink, varnishes. Besides, the time of a coating application on various areas of the object may be different and not corresponding to the initial creation time of the document, and due to the mutual effect of their coating and the substrate determination of the age of a substrate made of a cellulose-containing material including different types of cellulose and different by the composition on the basis of study of one index is insufficient, and using of several methods of testing associated with sampling by distractive methods leads to damage of the document or article. Thus in the described method taking the samples leads to violation of integrity of the tested article.

Therefore, so far there are no methods of determination and criteria of a simultaneous total estimation of parameters of the cellulose state in a cellulose-containing material on different areas of an object, both unprotected and protected in a different level of environmental effects, thereby stipulating the age and time of the event of coating application thereon, without a labour-consuming estimation of changes of the physical and chemical properties of the applied coatings and without violation of the article integrity.

Therefore, the problem of creation of a method for determination of the remoteness of an event of creation of a man-made object made of a cellulose-containing material or a man-made object fragment made of a cellulose-containing material having different elements of coatings, and a method for determination the remoteness of the event of such coating application on the surface of the cellulose-containing material is very actual.

Besides, the problem of determination of the remoteness of event of creation of a man-made object is intimately connected to the problem of protection of a man-made object from falsification of the remoteness of its creation because the existing methods of counterfeit detection are basically connected with taking off a large enough sample of the man-made object material that leads to violation of its integrity, and also associated with a labour-intensive process of studying the properties of the material and coating in their aging and changing under the environmental effects.

SUMMARY OF THE INVENTION

An object of the invention is to develop a method for determination of a remoteness of an event of creation of a man-made object made of a cellulose-containing material or a man-made object having on its surface fragments made of a cellulose-containing material and having surface areas with no coating and areas with a coating by means relative estimation of the changes in the properties of the cellulose in surface layer of the cellulose-containing material at creation of the man-made object and its changed state after creation of the man-made object and after application of the coating by means of measured and calculated parameters determined at the moment of study taking into account the dependence of such changes on the change of the coating state and on the varying conditions of the environment. Another object of the invention is to create a mark to be applied on the man-made objects or on its fragment during their making, allowing one to identify the remoteness of their creation without violating the integrity of the man-made objects and providing a possibility of protection of the man-made objects against falsification of their remoteness.

A first embodiment of the present invention relates to a method for determination of a remoteness of an event of creation of a man-made object made of a cellulose-containing material and having on its surface the coated areas with a coating and uncoated areas wherein on the basis of the results of measurements of the components and parameters of cellulose taken from the cellulose-containing material surface layer samples on each said area, including the free induction signal's parameters such as: the relaxation time $T_{2M}$ and $T_2$, accordingly, of the short and long components of the free induction signal, microseconds; the maximum amplitude $A_K$ and $A_D$, accordingly, of the short and long component of the free induction signal, degrees, and the density of protons $Pr_1$, $Pr_2$ in the cellulose taken from the cellulose-containing material surface layer samples on the uncoated and coated areas, accordingly, $g/cm^3 \cdot 10^6$, calculate $K_1$ and $K_2$ which are degrees of crystallinity of the cellulose from the uncoated and coated areas, accordingly, by the common formula:

$$K=1-5(T_{2M}*A_D/T2*A_K),$$

calculate the values of $G_1$ and $G_2$ which are relative changes of the cellulose parameters in each pair from uncoated and coated areas, accordingly, at a time $t_1$ of starting the analysis and at time $t_2$ after a predetermined time interval $\Delta t=t_2-t_1$, relative units, by the common formula:

$$G=K_2/K_1+Pr_2/Pr_1, \text{ and}$$

carry out the determination of the remoteness D of an event of a man-made object creation using the straight-line dependence functions G(D) of the relative changes G of the cellulose parameters in each pair from uncoated and coated areas on the remoteness D of the event of said coated area creation from beginning at the time point of the remoteness D=0 when G=0 to end at the time point $t_1$ of starting the analysis on D-axis corresponding to said each area pair, when the above relative changes $G_1$, $G_2$ were calculated for each pair from uncoated and coated areas at the time points $t_1$ and $t_2$, accordingly, and said each function G(D) has the angle $\alpha$ of slope of the straight-line function G(D) to the D-axis value-based on tg $\alpha=(G_2-G_1)/\Delta t$, and the value of D is calculated using formula:

$$G(D)=[(G_2-G_1)/\Delta t] \cdot D,$$

where for $G_1$ at time point $t_1$: $D_1=G_1/[(G_2-G_1)/\Delta t]$ and for the case when the value of the remoteness $D_1$ of the event of said coated area creation corresponding to each said areas pair are the same the conclusion made up of the remoteness D of event of the man-made object creation is the same too and for the case when the value of the remoteness $D_1$ of the event of said coated area creation corresponding to each said areas pair are different the conclusion made up of the remoteness D of event of the man-made object creation is related with possibility of detect any areas made by allowed or unwarranted interference in the said man-made object surface after its initial preparation.

In so doing, according to the invention, it is reasonable that in the said method for determination of the remoteness of an event of creation the measurements of said components and parameters of the cellulose samples are performed with the help of the nuclear-magnetic resonance spectrometry.

In so doing, according to the invention, it is reasonable that the sample of surface layer under a coating is taken from a highest coating density area.

Besides, according to the invention, it is reasonable that the samples having a minimum thickness of 0.05 mm and an area of not less than 0.3 $mm^2$ are used.

In so doing, according to the invention, it is reasonable to study samples of the coated areas coated with material selected from the group consisting of: colouring agents; varnishes; putties; art colors; typographical colours; stamp colors; pastes, for example, for ball pens; mastics, for example, for stamps; powders, for example, for cartridges of printing devices; ink, for example, for pen, capillary, gel pens, fountain pens and felt pens; indian ink; biopolymeric ink for pens.

In so doing, according to the invention, it is possible that said man-made object is a finished product or a fragment thereof.

In so doing, according to the invention, it is possible that the man-made object is a identification mark of remoteness of an event of its creation on the surface of a finished product or a fragment thereof, said mark having the coated areas made when said mark is secured on said surface by means of permanent connection with a possibility to get the cellulose-containing material samples from each said areas without the mark destruction and said method is used for determination of the remoteness D of the event of the man-made object creation according the remoteness of the coated areas creation on a mark surface.

In so doing, according to the invention, it is possible that the man-made object is made of a material comprising the cellulose selected from the group consisting of: cotton, flax, wood wherein the object is made of a material cellulose, selected cotton, flax, wood of deciduous and/or coniferous breeds, helm, papyrus, bamboo, rice or wheaten straw.

In so doing, according to the invention, it is possible that the man-made object is made of a paper.

In so doing, according to the invention, it is possible that the man-made object is made of paper selected from group consisting of: offset paper, newspaper, advertisement paper, cream-laid paper, vellum paper, Chinese paper, coated paper, elephant paper, rice paper, tracing paper, pergament paper, a Whitman paper a blotting paper, toilet paper, parchment paper, watermarked paper, wall-paper.

Besides, according to the invention, it is possible that the man-made object is made of cellulose-containing fibers.

In so doing, according to the invention, it is possible that the man-made object is made of woven or a knitted fabric selected from the group including: cottonous fabric, cotton cloth, rayon fabric, gobelin tapestry.

Besides, according to the invention, probably that the man-made object is made of a papier-mache.

Besides, according to the invention, probably that the man-made object is made of wood or wood-shaving materials.

Besides, the invention provides creation of an identification mark of a remoteness of the event of its creation on a surface of a finished product or a fragment thereof. The identification mark is made of a cellulose-containing material and adapted for tight fixation on the surface by means of a permanent connection providing destruction of the mark at its unauthorized removal from the surface, and has on the external surface the uncoated areas with no coating and the coated areas with a coating applied when the mark is fixed onto the surface. The mark is made with capability to get the cellulose-containing material samples from the surface layer of said mark surface areas suitable for the measurements of the cellulose parameters, including parameters of free induction signals and density of protons, on said uncoated area surface and under the coating of the coated area surface without the mark destruction.

The third embodiment of the present invention relates to a method for protection of a finished product or a fragment thereof against falsification of the remoteness of event of its original creation, wherein the identification mark made as described above is fixed by tightly securing it on the surface of the finished product or a fragment thereof by means of permanent connection when said finished product or a fragment thereof is prepared.

Thus, according to the invention, it is reasonable that a mark is made of a cellulose-containing material selected from the group consisting of: paper, fabric, papier-mache.

Thus, according to the invention, the coating on the surface of the fixed mark can be applied by means of a material selected from the group consisting of: colouring agents; varnishes; mastics; art colors; typographical colours; stamp colors; mastics; powders, for cartridges of printing devices; indian ink; biopolymeric ink for writing pens.

Thus, according to the invention, the mark can be fixed on the surface by means of an adhesive, varnish or paint.

BRIEF DESCRIPTION OF THE DRAWINGS

The present invention is further described by examples of realisation of a method for determination of the remoteness of an event of creation of a man-made object made of a cellulose-containing material having on its surface the first areas exposed to the environment and the second areas with a coating preventing environmental effects and by examples of making an identification mark of remoteness of the event of its creation on a surface of a finished product or a fragment thereof, and by examples of protecting a finished product or a fragment thereof against falsification of remoteness of event of its original creation and appended drawings, in which.

Figure 1:
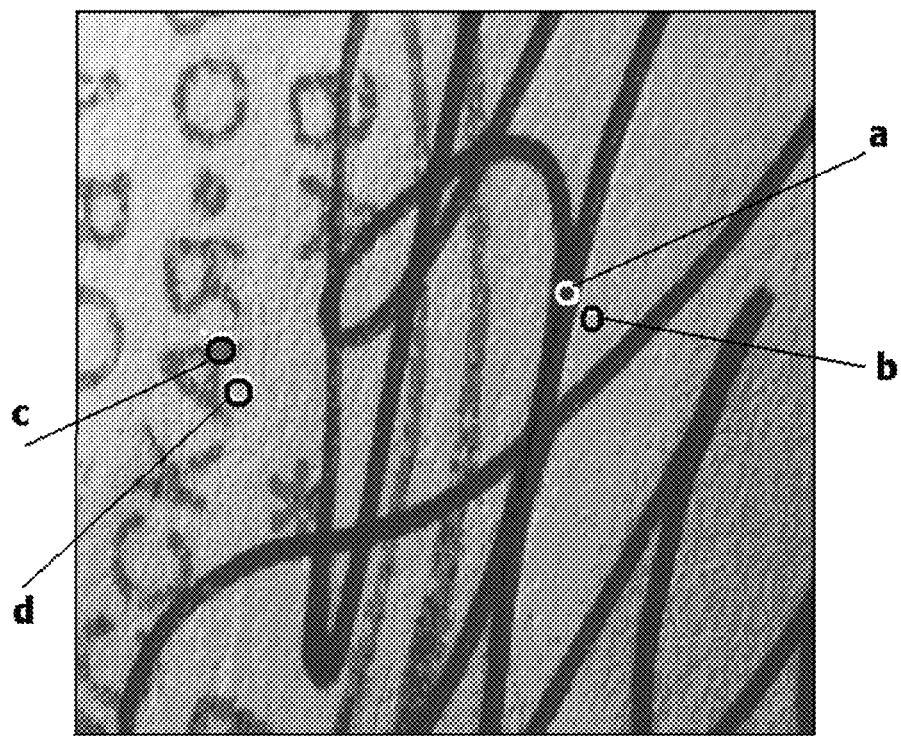
FIGS. 1, 2 illustrate the sampling to be tested by the method according to the invention.

The given examples are not exhaustive and are not beyond the set of claims.

DETAILED DESCRIPTION OF THE INVENTION

It is well known that cellulose is a natural biopolymer. The supermolecular structure of cellulose is extremely complex, it is determined by the ratio of crystalline and amorphous regions, each field having specific heterogeneity and accessibility. Eventually, the environmental and physical and chemical effects result in structural changes of the cellulose, its amorphicity (loosening): the amount of the crystalline regions decreases and, as a consequence, the area of amorphous regions increases.

In so doing as mentioned above, from the study of the cellulose structure by means of impulse nuclear-magnetic spectroscopy there were found multiple stages of the NMR-relaxational of the function consisting of two components: a short fast-relaxing component and a long slowly-relaxing one.

It is also known that the structural characteristics of cellulose are mainly determined by the short component of the relaxational function which carries information on the volume-mass dependence of the crystalline and amorphous phases of the polymer that allows one to determine not only the degree of crystallinity, but also to estimate the average size of crystalline and amorphous regions, as well as their bulk density.

It is also known that the spin-spin relaxation time sensitively reacts to changes of the molecular system in the elemental links of the cellulose molecules: the measurement of the amplitude of a free induction signal (FIS) and the spin-spin and spin-lattice relaxation time allow us to obtain information on the cellulose state and properties and their change as a result of various physical and chemical effects.

On the basis of the modern concept of the nuclear-magnetic relaxation in multiphase systems methods for determining specified key parameters on the basis of measurements of the free induction signal (FIS), for example, by means of impulse spectroscopy NMR have been developed.

Also it is known that the amount of protons depends on the state of the cellulose molecules: destruction of the molecules leads to release of the protons. In so doing the density Pr of distribution of protons is determined by the actual data of measurements by means of NMR spectroscopy.

Thus the key parameters characterising the microstructure of the cellulose and its derivatives, their physical and chemical state and change of these cellulose properties are specified by:

the degree of crystallinity of the cellulose;
the density of distribution of protons (an amount of protons).

Known in the art is a method for determining the degree of crystallinity of cellulose from the results of measurements of the amplitude of the free induction signal (FIS) and the time of the spin-spin and spin-lattice relaxation (NMR capability in the analysis of structural and sorption properties of biopolymers. Grunin Yu. B. et al by calculation using the formula:

$$K=1-5(T_{2M} \cdot A_D / T_2 \cdot A_K), \qquad (1)$$

where: $T_{2M}$ and $T_2$ are spin-spin relaxation times, accordingly, strongly connected and relatively weakly connected by a water sample, in microseconds;

$A_K$ and $A_D$ are the amplitudes of the short and long components of the free induction signal (FIS) with relaxation times $T_{2M}$ and $T_2$, accordingly, degrees.

Experimentally by means of standard methods of NMR spectroscopy on impulse NMR of the spectrograph of the company AVANCE AV300 (Germany) measurements of specified values of parameters characterising a physical and chemical and structural state of various types of initial raw cellulose for manufacture of a cellulose-containing material were carried out as shown in Table 1, which can be used for carrying out a comparative analysis of the cellulose properties in the process of its aging under the environmental effects.

TABLE 1

Values of the physical and chemical and the structural parameters of original raw cellulose various types applied in manufacture of some cellulose-containing materials.

| | Type of raw cellulose in a cellulose containing material | | | | |
|---|---|---|---|---|---|
| Parameter | Unbleached sulphate cellulose | Cotton cellulose | Bleached sulphite cellulose | Unbleached sulphite cellulose | Refined sulphite cellulose |
| Relaxation time of the short FIS component, $T_{2M}$, microseconds | 59 | 60 | 65 | 58 | 62 |
| Relaxation time of the long FIS component, $T2$, microseconds | 1640 | 2000 | 1540 | 1470 | 1230 |
| Maximum amplitude of the short FIS component, $A_K$, degree | 122 | 120 | 131 | 127 | 114 |
| Maximum amplitude of the long FIS component, $A_D$, degrees | 137 | 160 | 148 | 153 | 110 |
| Calculated degree of crystallinity, K relative units | 0.798 | 0.8 | 0.76 | 0.755 | 0.757 |

From the data given in Table 1 it follows that the initial virgin cellulose obtained by various methods from different natural raw at positioned distinction of values of amplitudes of a free induction signal (FIS) and the time of the spin-spin and spin-lattice relaxation has almost identical degree of crystallinity K, determined by formula 1 on the basis of the measurements made with the impulse NMR spectroscopy that allow one to use the measurements of the amplitudes and the relaxation time of short and long FIS components as distinctive characteristics of the state and structure of cellulose of any type. And it is clear that the results of these measurements characterize the state and volume of crystalline and amorphous regions of cellulose.

The same parameters and for different other types of virgin cellulose used for obtaining of the cellulose-containing materials can be determined in the same way.

For a long time the inventor had been studying a large quantity of samples of different man-made objects made of cellulose-containing materials based on different types of cellulose having a general formula $[C_6H_7O_2(IT)_3]_n$. In so doing the man-made objects and their fragments having on its surface various areas with different coatings with well known remoteness of its creation more than 15 days and kept under different conditions have been studied: under normal conditions or in premises with a known particular regime of storage, for example, in archives and in museums. In so doing different objects have been studied:

man-made objects made of a cellulose-containing material, in particular, based on cellulose sulphate bleached, sulphate unbleached, sulphite bleached and sulphate unbleached, obtained from different natural sources of cellulose: from cotton, from wood and a bark of coniferous or deciduous breeds, from rice and wheaten straw, from a flax, straw, from the papyrus, from bamboo, in the form of different articles, in particular, books, booklets, newspapers, logs, posters, manuscripts, wall-paper, cards, printed and hand-written letters, financial and notarial documents with printed text and hand-written elements, made on different cellulose-containing paper: advertisement paper, Whatman paper, vellum paper, cream-laid paper, watermarked paper, newspaper, tracing paper, kraft paper, coated paper, offset paper, pergament paper, blotting paper, rice paper, elephant paper, toilet paper;

man-made objects made of fibers containing cellulose cottonous or cellulose material; from wood of deciduous and coniferous breed, in the form of different cottonous and rayon fabrics, articles of clothes, articles of an interior, gobelin tapestries;

man-made objects made of papier-maches based on cellulose of different types, in the form of souvenir articles, relief overlays on picture frames, for furniture;

man-made objects made of wood of coniferous and deciduous breeds in the form of furniture articles, articles of an interior, a sculpture;

man-made objects of wood-shaving materials in the form of panels;

man-made objects in the form of the identification mark made of masses of papier-mache based on cellulose of different types, then solidified in air, from paper scrap, from a scrap of fabric and glued onto the surface, varnish or colour on articles of marble, on a grounded canvas, on the face and back of pictures painted by oil and water colours, on wooden articles;

In so doing the man-made object in the form of a finished product or a fragment thereof had surface coated areas made by different contact methods, characterized by a different degree of filling of the surface layer of an man-made object material: by application on paper by the hand-written method, a letterpress printing, offset printing, stamping; by application on a fabric by straight-line and sublimatic heat transfer printing, a manual method.

In so doing the coatings have been selected from the group consisting of: colouring agents; varnishes; mastics; art colors including oil, a water colour, gouache; typographical colours; colours and mastics stamp; pastes for ball pens; powders for cartridges of printing devices; ink for pen, capillary, gel, fountain pens and felt pens; indian ink; biopolymeric ink for pens.

The man-made objects in the form of identification marks had a different shape and size in a range of 0.3 to 1.0 cm². In so doing the identification marks from a papier-mache material have been applied on the surface of man-made objects in the form of round drops with subsequent hardening of the papier-mache after in air and application of the coating on a part of their surface. The identification marks of fabric and paper have been made in the form of strips on their part of whose surface the coating in the form of dash samples or circles has been applied and fixed on the man-made objects surface by means of glue or varnish or oil colour. In so doing the coating on all the identification marks has been applied by means of a material selected from the group consisting of: colouring agents; varnishes; mastics; art colors; printing ink; stamp colors; mastics; powders for cartridges of printing devices; indian ink; biopolymeric ink for pens.

In the course of carrying out the study for preparing the samples of surface layer of a cellulose-containing material to be tested were taken from the uncoated areas exposed to the environment and the coated areas with a coating preventing environmental effects in the form of disks having a diameter in a range of 0.3 to 0.55 mm and a thickness of not less than 0.01 mm by means of the tool of a pinching tool having an internal opening with a diameter no more than 0.6 mm.

Figure 2:
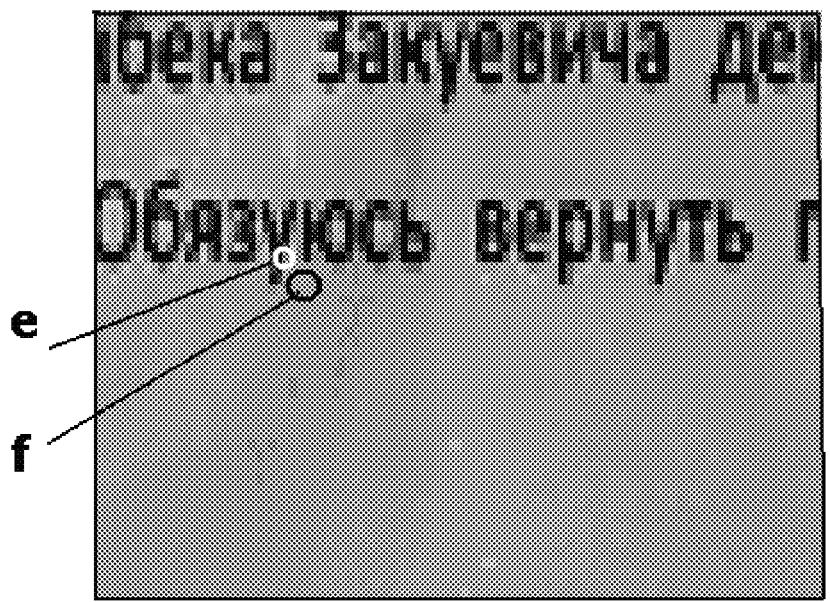

In so doing said samples were taken from the areas having the greatest density of the coating among all areas available on the man-made object surface with one type of the coating, and said samples were taken on the said areas neighbouring location, for example, as shown in FIG. 1 and FIG. 2, where "a", "c" and "e" are the areas of cutout of samples of the surface layer of the cellulose-containing material under the coating on the second areas coated of stamping ink, paste a ball pen ink and a toner powder, accordingly, «b» «d» and «f» are the first areas of cutout of samples of the surface layer of the cellulose-containing material with no coating.

In the course of study called the objects to be tested under a microscope for determining the areas for taking samples of a cellulose-containing material.

Then a cellulose sample was extracted from each cellulose-containing material sample under a microscope, each cellulose sample was placed in an individual clean test tube and placed in an impulse NMR spectrometer.

Using the well known methods of impulse nuclear-magnetic spectrometry, the following measurements were made:
time $T_{2M}$ of relaxation of the short FIS component;
time $T_2$ of relaxation of the long FIS component;
the maximum amplitude $A_D$ of the long FIS component;
the maximum amplitude $A_K$ of the short FIS component,
the density $Pr_2$ of protons in the cellulose on the area under a coating, the density $Pr_1$ of protons in the cellulose on the area having no coating.

The degree of crystallinity $K_1$ of the cellulose on the area with no coating and degree of crystallinity $K_2$ of the cellulose on the area with a coating were calculated by the formula:

$$K=1-5[T_{2M}*A_D)/(T_2*A_K)], \quad (1)$$

where: $T_{2M}$ is the relaxation time of the short FIS component, microseconds;
$T_2$ is the relaxation time of the long FIS component, microseconds;
$A_D$ is the maximum amplitude of the long FIS component, degree;
$A_K$ is the maximum amplitude of the short FIS component, degree.

Then there were determined the relative change value $K_2/K_1$ of crystallinity degree $K_2$ of the cellulose extracted from the sample taken of said area with a coating in comparison with the crystallinity degree $K_1$ of the cellulose extracted from the samples taken of said uncoated area which characterizes the changes of the cellulose structure depending on the environmental effects and the level of natural aging of the cellulose.

In addition, there were determined the relative change value $Pr_2/Pr_1$ of the proton density $Pr_2$ of the cellulose from the coated area with a coating, in comparison with the density $Pr1$ of protons in cellulose area having no coating, which also characterizes the changes in the cellulose structure depending on the environmental effects and a degree of the natural aging of the cellulose.

Then there was calculated the value G of relative changes of this cellulose parameters characterising the changes in cellulose structure depending on the environmental effects and a degree of the natural aging of the cellulose based on the changes in the degree of crystallinity K and changes of the density Pr of protons for each tested sample of the cellulose containing material under the following formula according to the invention:

$$G=K_2/K_1+Pr_2/Pr_1, \quad (2)$$

where:
K1 is the degree of crystallinity of the cellulose area having no coating, relative units;
K2 is the degree of crystallinity of the cellulose area with a coating, relative units;
Pr1 is the density of protons of the area having no coating, g/cm3·10⁶;
Pr2 is the density of protons in the coated area, g/cm3·10⁶.

The above measurements and calculations were for studied man-made objects with a given periodicity six times a year in a 2-months interval.

Based on the obtained values of G for each tested man-made object whose remoteness was known to the inventor, graphics were plotted in coordinates: on the axis «y»—G at the instant of time $t_1$ and $t_2$, in relative units, on the «x» axis—the time D corresponding to the time which had passed from an event of tested object the date of the beginning of study, in months. As a unit for the «x» scale can be made of other time units, however, the most acceptable unit for determination of the reliable values of the cellulose parameters and relative changes of these parameters is time in months.

In the course of the analysis of the results of measurements and by mathematical computations on the basis of the obtained experimental data a linear dependence G (D) was found for all studied objects and the samples having a different slope to the «x» axis depending on the type and density of the coating and the gradient of speed of change of the cellulose parameters in time:

$$G(D)=[(G_2-G_1)/\Delta t]\cdot D, \quad (3)$$

where: $G_1$ and $G_2$ are the relative values of changes of the parameters of the tested cellulose samples, accordingly, in the previous and subsequent studies, relative units;

Δt is the time interval between the previous and subsequent studies, months;

D is the time dating event of test object creation, months.

In this case, the dependence $(G_2-G_1)/\Delta t$ characterizes the angle α of slope of the straight-line G (D) to the «D» axis depending on the gradient of the relative changes in the cellulose parameters of the coated areas in comparison with the changes of the cellulose parameters in the areas with no coating that is resulting of a change of the density and transitivity of the coating and processes decreasing the protection of the surface of the cellulose-containing material from the external effects and degradation of the coating.

Figure 3:
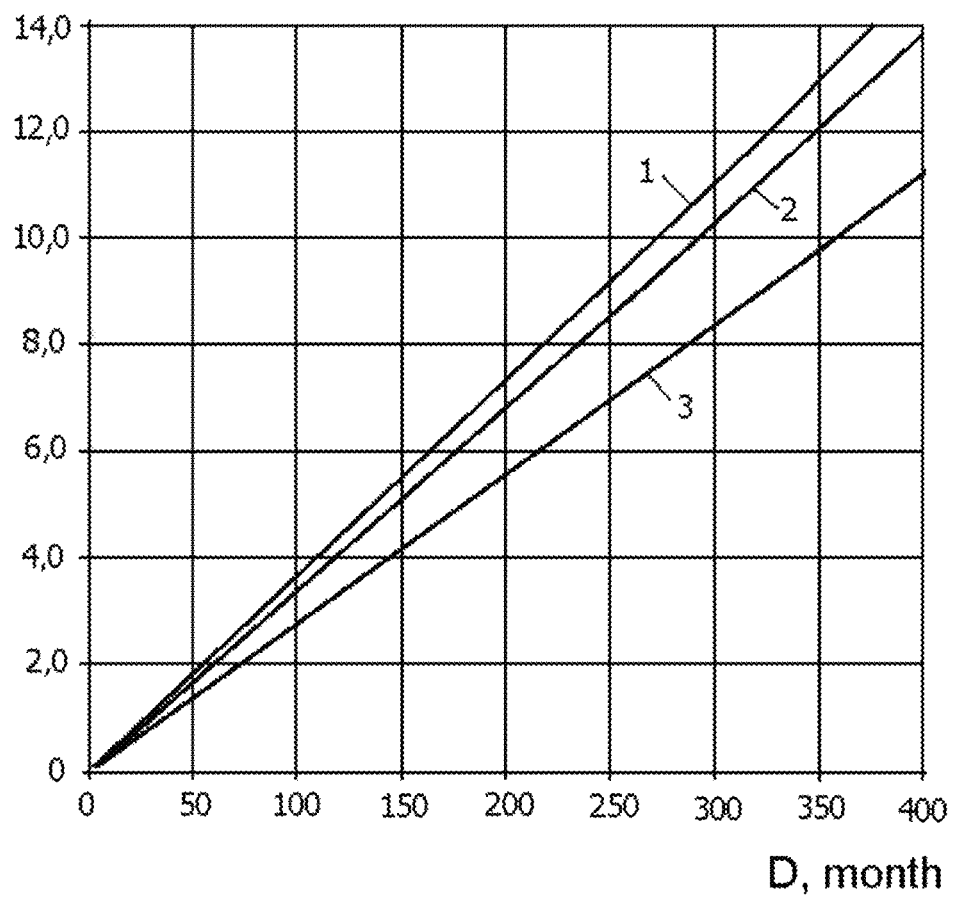
FIG. 3 illustrates the straight-line dependence function G (D) of aging of different man-made objects, obtained on the experimental data basis.

FIG. 3 illustrates some typical dependencies G(D) for various said tested cellulose-containing man-made objects which were determined by the method according to the invention on the basis of experimental data, for example, straight-lines 1, 2 and 3 for the finished product based on bleached sulphite cellulose with coatings applied thereon:

straight-line 1 represents dependence G=0.0369 D determined:
for a man-made object made in the form of a document on offset paper and having in the field a printed text made by means of a laser printer with a powdery toner of black color;
for a man-made object made in the form of a document on an offset paper and having in the field graphical characters applied by ink for a gel pen;
for a man-made object made in the form of a picture by a china ink on rice paper;

straight-line 2 represents dependence G=0.0338 D, determined:
for a man-made object made in the form of a document on an offset paper and having in the field graphical characters, applied by ball pen paste;
for a man-made object made in the form of a picture made by gouache on a Whatman paper;
for a man-made object made in the form of a picture made by a water color on a Whatman paper;

straight-line 3 represents dependence G=0.0277 D, determined:
for a man-made object made in the form of a document on laid paper having an ink signature applied with a fountain pen;
for a man-made object made in the form of a document on an elephant paper having in the field an impress of a seal applied by stamping ink.

Thus, the straight-linear dependencies G(D) determined in formula 3 for each tested man-made object can be used, according to the invention, for the measured cellulose parameters $Pr_2$, $Pr_1$, $T_{2M}$, $A_D$, $T_2$, $A_K$ and the values $K_2$ and $K_1$ calculated by formula 1 can be used for copulation of the value G by formula 2 and on the line a point can be found that corresponding to this value G and having appropriate remoteness D of creating a tested area with a coating on the tested man-made object, and in case of coincidence of determination of the remoteness D of the event of said coated area creation at said regions for all coated areas, a conclusion may be made on creation of a man-made object as a whole.

Figure 4:
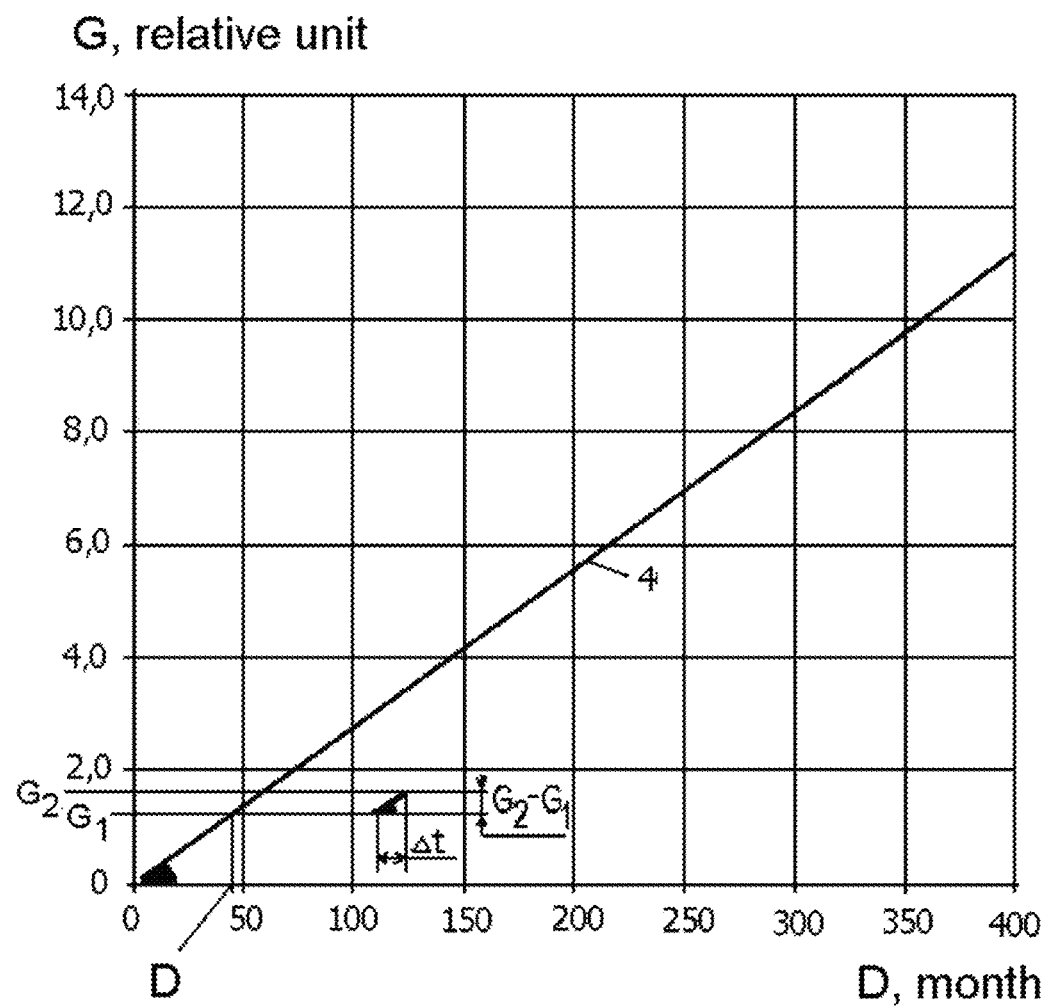
FIG. 4 is a scheme of plotting the straight-line dependence function G (D) and determination of the remoteness D by the calculated value G of the relative changes of cellulose parameters of cellulose-containing materials in the areas with a coating and the areas with no coating.

The scheme of building up a straight-line 4 for determination of the remoteness of event of creation of each of coated areas of the tested man-made objects and determination of D are shown on FIG. 4. For this purpose, at any place of a grid chart a segment $G_2-G_1$ was plotted, the values $G_2$ and $G_1$ calculated by formula 2 on the basis of the results of measurements at the second and first study (subsequent and previous), accordingly, and the segment ends were spaced from each other for a certain distance corresponding to the time interval Δt between the first and second studies of the samples taken from areas with and with no coating. By the slope of said segment the angle of slope of the line 4 to the «x» axis with a peak at the point G=0 at D=0 was determined. The line 4 was then built up by the value $G_1$ of the first study, and on the line 4 the inventors found an appropriate point with a coordinate y–G1 and calculated its coordinate on the «x» axis corresponding to the time D of creation of a test area with a coating.

If all coated areas have identical remoteness of the event, a conclusion may be drawn as to the remoteness of the event of creation of an object as a whole. If the remoteness of the creation event of various areas was different, a conclusion may be made on interference in the object after its initiating creation.

The given comparison of the values G calculated by formula 2 for the coated second areas on the tested man-made objects having the remoteness D of the event of their creation known to the experts, and the values G obtained for this remoteness D of their creation from the experimental straight-line and by formula 3 have shown the complete convergence of the results.

Thus, during the creation of the invention, the inventors had found dependencies determining the degree of change of the properties and characteristic of the cellulose parameters with account of the degree of change of the coatings with time allowed to estimate the dating events of creation of individual areas and an man-made objects as a whole without study of coatings themselves but only on the basis of the studies of the cellulose parameters, using them for comparative analysis of the coated and uncoated areas properties. In so doing the found dependencies allowed the development of a method for determination of the remoteness D of an event of man-made objects creation as a finished product comprising cellulose in the material of which a finished product is made, or comprising cellulose in individual fragments of a finished product, or individual elements in form a mark comprising cellulose and allocated on the surface of the a finished product or its fragments.

Specialists in the field of technical investigation for criminalistic and judicial expertise understand that when the object is a fragment of a finished product or a mark made of a cellulose containing material having opened areas with no coating and an area with a coating, it is possible to determine the remoteness of creation event of such a fragment or the remoteness of applying a mark on their areas.

In so doing, according to the invention, the fragment of the finished product or a mark can be made integrally with the finished product or separately from the finished product and also made of a cellulose-containing material or another materials, and fixed to the finished product surface by permanent connection, for example, by means of an adhesive that allows one to use such a fragment or such a mark as an element identifying the finished product remoteness of event of creation.

Thus, according to the invention, the identification mark can be made of papers, fabrics, papier-mache or other materials based on cellulose and having an area with a coating, for example, a pointwise coating. The identification mark can be made in the form of a volumetric or plane figure of a different shape with an image including an identified element visually or under a microscope, for example, in the form of a trade mark of the author of an article and/or a trade mark of the owner of an article and/or a trade mark of the manufacturer or in the form of an identified index of the finished product.

Determining the remoteness of a man-made object creation by the date of plotting the identification mark by the method according to the invention including study of microscopic samples taken of the areas of the mark surface without its destruction allows one to determine the remoteness of event of coating application on the mark surface in the form of an image and the remoteness of event of plotting said mark on man-made object surface that allows one to draw a conclusion on authenticity of the man-made object or on the forgery made in a later period. Those skilled in the art understand that the use of such marks is important in antiquarian and museum activity, as well as in a notariate and at creation of historically important documents which are subject to storage for an unlimited period.

Creation of a method for determining the remoteness of event of man-made object creation according to the invention and creation of the identification mark according to the invention has resulted in creation of a method for protection of man-made object against falsification of the remoteness of event of its creation by plotting an identification mark on its surface allowing one to identify the date of creation of the man-made object, in which the remoteness of event of mark creation on the man-made object surface made of a cellulose-containing material and fixed to the man-made object surface by means of a permanent connection providing destruction of the mark at its unauthorized removal from the surface, and provide the presence on its external surface of some areas having no coating and areas with a coating applied when the mark is fixed to the surface, for example, by means of an adhesive, a varnish or a paint.

The marks can be made of a cellulose-containing material selected from a group consisting of: paper, fabric, papier-mache, and the coating on the surface of the fixed mark can be applied by means of a material selected from a group consisting of: coloring agents; varnishes; mastics; color art; printing blacks; stamp colors; mastics; powders, for example, for cartridges of printing devices; indian ink; biopolymeric ink for pens.

The validity of the results of determination of remoteness of the event of creation of man-made object having unknown remoteness were vested by unknown owners for determination of remoteness of the event of its creation by means of standard techniques using the method of determination of remoteness according to the invention:

man-made object No 1 made in form of fragment of printed paper document made of paper comprising bleached sulphite cellulose and having on one side a printed words made with unknown composition toner by laser printer, with the words relating to the document creation remoteness as "10.08.2000" and the signature made by ball pen and the impress of a seal made with unknown composition blue mastic in form of round image;

man-made object No 2 made in form of statuette made, as it was determined by the inventor by means of standard techniques, of cellulose-containing papier-mache having the first areas with no coating and the second areas plated with unknown composition dye on statuette surface; The statuette had on the surface areas a coating in the form of image elements made by color of unknown type and composition;

object No. 3 in the form of a gobelin tapestry made, as it was determined by the inventor by means of standard techniques, of threads bases on the cottonous fibers, colored by applying a coloring agent on the surface with a varying density and having screw weaving;

object No. 4 in the form of a furniture article made, as it is determined by the inventor by means of standard techniques, of wood of deciduous breed—beech and having on the front face a lacquer coat of unknown composition and below an inlaid insertion made of a cedar.

The results of the study of objects Nos. 1-4 and the results of determination of the remoteness of the event of creation of the tested man-made object as whole and the remoteness of event of creation on their surface of coated areas by the claimed method are presented in Tables 2 to 5.

TABLE 2

Example of determination of remoteness of the event of creation of said object No. 1 and creations of coated areas thereon using the method according to the invention

| | | Tested object No. 1 | | | | |
|---|---|---|---|---|---|---|
| No. | Measured and calculated parameters | Area of an area of the document having no coating | Printed text having a paper coating made with toner | Hand-written signature made by a ball pen of blue dark colour | Impress of a seal made by dark blue stamping ink | Reference: parameters of bleached sulphite cellulose used at production of the paper |
| 1 | The relaxation time of the short FIS component measured in the first study and measured in the second study $T_{2M}$, microseconds | 63/60 | 58/59 | 64/65 | 61/63 | 65 |

TABLE 2-continued

Example of determination of remoteness of the event of creation of said object No. 1 and creations of coated areas thereon using the method according to the invention

| | | Tested object No. 1 | | | | |
|---|---|---|---|---|---|---|
| No. | Measured and calculated parameters | Area of an area of the document having no coating | Printed text having a paper coating made with toner | Hand-written signature made by a ball pen of blue dark colour | Impress of a seal made by dark blue stamping ink | Reference: parameters of bleached sulphite cellulose used at production of the paper |
| 2 | The relaxation time of the long FIS component measured in the first study/measured in second study, $T_2$, microsec | 1110/1070 | 1570/1580 | 1450/1430 | 1216/1175 | 1540 |
| 3 | The maximum amplitude of the short component FIS measured in the first study and measured in the second study, $A_K$, degree | 96/109 | 134/129 | 108/112 | 116/122 | 131 |
| 4 | The maximum amplitude of the long component FIS measured in the first study and measured in the second study, $A_D$, degree | 130/149 | 148/147 | 131/138 | 126/132 | 148 |
| 5 | The degree of crystallinity of cellulose of the area having no coating, calculated in the first study and calculated in the second study, $K_1$, relative units | 0.61347/0.62013 | — | — | — | 0.76 |
| 6 | The degree of crystallinity of cellulose of the area with a coating, calculated in the first study and calculated in the second study, $K_2$, relative units | — | 0.79571/0.78723 | 0.73231/0.72003 | 0.7251/0.71005 | — |
| 7 | The density of protons on the area having no coating, measured in the first study and measured in the second study, $Pr_1/cm^3 \cdot 10^6$ | 1.63730/1.58087 | — | — | — | — |
| 8 | The density of protons on the area with a coating, measured in the first study and measured in the second study, $Pr_2$, $g/cm^3 \cdot 10^6$ | — | 3.28716/3.47001 | 3.05370/3.12015 | 2.99983/3.13007 | — |
| 9 | The value of the relative changes of the parameters of cellulose: G1, calculated by formula 2 in the first study/$G_2$ in the second study, relative units | — | 3.02409/3.05183 | 3.07957/3.10731 | 3.07924/3.10698 | — |
| 10 | Time interval between the first and second study, $\Delta t$, microsec | 1 | 1 | 1 | 1 | — |
| 11 | Ratio $(G_2 - G_1)/\Delta t$ for plotting the line | — | 0.02774 | 0.02774 | 0.02774 | — |
| 12 | The remoteness of event of creation determined by formula 3 for the value G, calculated by formula 2 in the first study and/determined by the line D, months | — | 109/109 | 111/111 | 111/111 | — |

Thus, as seen from Table 2, the claimed method was used for determining in the tested object No. 1 the following results:

remoteness of the event of creation of printed text on paper constituting 109 months, remoteness of the event of creation a signature on paper constituting 111 months, remoteness of the event of creation of an impress of a seal constituting 111 months.

On the basis of the obtained results the following conclusions may be drawn:

the signature and impress of a seal on the document have been made nine years three months till the moment of the first expert study;

the printed text on the document has been made nine years one month till the moment of the first expert study;

hence, the signature and impress of a seal have been made 2 months prior to making the printed text, and the remoteness of the event of document creation dated of Aug. 10, 2000 stated on the document does not meet the actual date.

The comparison of the obtained calculation results with the remoteness of events of creation of coated areas on the tested object No. 1 obtained on the basis of the experimental data has shown their convergence within one months.

TABLE 3

Example of application of the claimed method for determining the remoteness of the event of object No. 2 creation and of coated areas thereon creation.

| No | The measured and calculated parameters | Tested object No. 2 | | | Reference: parameters of unbleached sulphite cellulose used in said object |
|---|---|---|---|---|---|
| | | The area having no coating | The area with a white coating | The area with a red coating | |
| 1 | The relaxation time of short FIS component measured in the first study and measured in the second study, $T_{2M}$, microseconds | 45/42 | 57/56 | 60/58 | 62 |
| 2 | The relaxation time of the lFIS component measured in the first study and measured in the second study, $T_2$, microseconds | 1050/960 | 1210/1170 | 1190/1176 | 1230 |
| 3 | The maximum amplitude of short FIS component measured in the first study and measured in the second study, $A_K$, degrees | 62/55 | 92/86 | 102/92 | 110 |
| 4 | The maximum amplitude of the long FIS component measured in the first study and measured in the second study, $A_D$, degrees | 93/89 | 112/103 | 106/105 | 114 |
| 5 | The degree of crystallinity of the cellulose area having no coating, calculated in the first study and calculated in the second study, $K_1$, relative units | 0.6785/ 0.6460 | — | — | 0.8 |
| 6 | The degree of crystallinity of the cellulose area with a coating, calculated in the first study and calculated in the second study, $K_2$, relative units | — | 0.7133/ 0.7132 | 0.7380/ 0.7185 | — |
| 7 | The density of protons on the uncoated area measured in the first study and measured in the second study, $Pr_1$, g/cm$^3$ 10$^6$ | 0.29154/ 0.32985 | — | — | — |
| 8 | The density of protons on the coated area, measured in the first study and measured in the second study, $Pr_2$, g/cm$^3 \cdot 10^6$ | — | 2.82464/ 3.18957 | 1.95107/ 3.2 | — |
| 9 | The value of relative changes of cellulose parameters: G1, calculated by formula 2 in the first study and G2, calculated in the second study, relative units | — | 10.7400/ 10.7738 | 10.7800/ 10.8138 | — |
| 10 | Time interval between the first and the second studies, Δt, microseconds | 1 | 1 | 1 | — |
| 11 | Ratio $(G_2-G_1)/\Delta t$ for plotting line | — | 0.0338 | 0.0338 | — |

TABLE 3-continued

Example of application of the claimed method for determining the remoteness of the event of object No. 2 creation and of coated areas thereon creation.

| | | Tested object No. 2 | | | |
|---|---|---|---|---|---|
| No | The measured and calculated parameters | The area having no coating | The area with a white coating | The area with a red coating | Reference: parameters of unbleached sulphite cellulose used in said object |
| 12 | The remoteness of the event determined in formula 3 for the value G, calculated by formula 2 in the first study and determined by the line, D, months | — | 318/318 | 319/319 | — |

Thus, as shown in Table 3, the claimed method was used for determining in the tested object No. 2 the following results:

the remoteness of the event of creation of an area with a white coating constituting 318 months, the remoteness of the event of creation of an area with a red coating constituting 319 months.

On the basis of the obtained results the following conclusions may be drawn:

the area with the white coating was made 26 years 6 months prior to the moment of the first study;

the area with the red coating has been made 26 years 7 months prior to the moment of the first study.

Hence, the area with the white coating has been made for one month later than the area with the red coating that can be associated with updating the coating; in general, object No. 2 in the form of a figurine made of papier-mache as a whole, can be dated by time 26 years 7 months before the first study.

TABLE 4

Example of application of the claimed method for determining the remoteness of the event of object No. 3 creation and of coated areas thereon creation.

| | | Tested object No. 3 | | | |
|---|---|---|---|---|---|
| No | The measured and calculated parameters | The area having no coating | The area with coating, made with a low-intensity red coloring agent | The area with a red coating | Reference: the parameters of unbleached sulphite cellulose used in the man-made object |
| 1 | The relaxation time of the short FIS component measured in the first study and measured in the second study, $T_{2M}$, microseconds | 38/35 | 51/49 | 54/51 | 60 |
| 2 | The relaxation time of the long FIS component measured in the first study and measured in the second study, $T_2$, microseconds | 1230/1160 | 1960/1920 | 1980/1930 | 2000 |
| 3 | The maximum amplitude of the short FIS component measured in the first study and measured in the second study, $A_K$, degrees | 76/68 | 116/110 | 117/110 | 120 |
| 4 | The maximum amplitude of the long FIS component measured in the first study and measured in the second study, $A_D$, degrees | 89/83 | 142/139 | 145/137 | 160 |

TABLE 4-continued

Example of application of the claimed method for determining the remoteness of the event of object No. 3 creation and of coated areas thereon creation.

| No | The measured and calculated parameters | Tested object No. 3 | | | Reference: the parameters of unbleached sulphite cellulose used in the man-made object |
|---|---|---|---|---|---|
| | | The area having no coating | The area with coating, made with a low-intensity red coloring agent | The area with a red coating | |
| 5 | The degrees of crystallinity of the cellulose area having no coating, calculated in the first study and calculated in the second study, $K_1$, relative units | 0.8191/ 0.8158 | — | — | 0.8 |
| 6 | The degrees of crystallinity of the cellulose area with a coating, calculated in the first study and calculated in the second study, $K_2$, relative units | — | 0.8407/ 0.8387 | 0.8310/ 0.8260 | — |
| 7 | The density of protons on the area having no coating, measured in the first study and measured in the second study, $Pr_1$, g/cm$^3$ · $10^6$ | 0.16725/ 0.15273 | — | — | — |
| 8 | The density of protons on the area with a coating, measured in the first study and measured in the second study, $Pr_2$, g/cm$^3$ · $10^6$ | — | 2.01933/ 1.86066 | 2.02120/ 1.86295 | — |
| 9 | The value of relative changes of cellulose parameters: $G_1$, calculated by formula 2 in the first study and G2, calculated in the second study, relative units | — | 13.1001/ 13.2108 | 13.0995/ 13.2102 | — |
| 10 | Time interval between the first and second studies, $\Delta t$, microseconds | 3 | 3 | 3 | — |
| 11 | The ratio $(G_2 - G_1)/\Delta t$ for plotting the line | — | 0.0369 | 0.0369 | — |
| 12 | The remoteness of creation event determined in formula 3 for the value G, calculated by formula 2 in the first study and determined by the line, D, months | — | 358/358 | 358/358 | — |

Thus, as shown in Table 4, the claimed method was used for determining in the tested object No. 3 the following results:

the remoteness of the event of creation of an area with a low-intensity red coating constituting 358 months, the remoteness of the event of creation of an area with a low-intensity yellow coating constituting 358 months.

On the basis of the obtained results the following conclusions may be drawn:

the remoteness of event of creation of an area with a low-intensity red coating and remoteness of event of creation of an area with a low-intensity yellow coating are identical and constitute 29 years and 10 months, hence, the gobelin tapestry has been made 29 years and 10 months prior to the first study, and as a whole object No. 3 can be dated by 29 years and 10 months before the first study that completely corresponds to the information given by the owner later.

TABLE 5

Example of application of the claimed method for determination of the remoteness of event of object No. 4 and creation of coated areas thereon creations.

| No. | The measured and calculated parameters | Object No. 4 | | | Reference: parameters of wood cellulose used in the object |
|---|---|---|---|---|---|
| | | The area having no coating | The area of beech with a lacquer coat | The area with an insertion element made of cedar with a lacquer coat | |
| 1 | The relaxation time of the short FIS component measured in the first study and measured in the second study, $T_{2M}$, microseconds | 53/48 | 56/62 | 68/71 | 75 |
| 2 | The relaxation time of the long FIS component measured in the first study and measured in the second study, $T_2$, microseconds | 1056/1095 | 1150/1230 | 1340/1370 | 1430 |
| 3 | The maximum amplitude of the short FIS component measured in the first study and measured in the second study, $A_K$, degrees | 55/57 | 85/89 | 90/93 | 96 |
| 4 | The maximum amplitude of the long FIS component measured in the first study and measured in the second study, $A_D$, degrees | 103/110 | 115/118 | 120/122 | 127 |
| 5 | The degrees of crystallinity of the cellulose area having no coating, calculated in the first study and calculated in the second study, $K_1$, relative units | 0.63/0.53 | — | — | 0.8 |
| 6 | The degrees of crystallinity of the cellulose area with a coating, calculated in the first study and calculated in the second study, $K_2$, relative units | — | 0.733/0.665 | 0.661/0.660 | — |
| 7 | The density of protons on the area having no coating, measured in the first study and measured in the second study, $Pr_1$, g/cm$^3$ · 10$^6$ | 0.370/0.340 | — | — | — |
| 8 | The density of protons on the area with a coating, measured in the first study and measured in the second study, $Pr_2$, g/cm$^3$ · 10$^6$ | — | 3,2308/3.0549 | 3,3750/3.0578 | — |
| 9 | The value of the relative changes of the cellulose parameters: $G_1$, calculated by formula 2 in the first study and $G_2$, calculated in the second study, relative units | — | 10.172/10.240 | 10.171/10.239 | — |
| 10 | Time interval between the first and second studies, $\Delta t$, microseconds | 2 | 2 | 2 | — |
| 11 | The ratio $(G_2-G_1)/\Delta t$ for plotting the line | — | 0.0338 | 0.0338 | — |

TABLE 5-continued

Example of application of the claimed method for determination of the remoteness of event of object No. 4 and creation of coated areas thereon creations.

| | | Object No. 4 | | | |
|---|---|---|---|---|---|
| No. | The measured and calculated parameters | The area having no coating | The area of beech with a lacquer coat | The area with an insertion element made of cedar with a lacquer coat | Reference: parameters of wood cellulose used in the object |
| 12 | The remoteness of the creation event determined in formula 3 for the value G, calculated by formula 2 in the first study and determined by the line, D, months | — | 303/303 | 303/303 | — |

Thus, as shown in Table 5, the claimed method was used for determination in the tested object No. 4 the following results:
  the remoteness of the event of creation a deciduous breed-beech area with a lacquer coating constituting 303 months,
  the remoteness of the event of creation of an area with a cedar insertion with a lacquer coating constituting 303 months.

On the basis of the obtained results a conclusion may be drawn that the method for determination of the remoteness of an event of creation of a man-made object made of a cellulose-containing material is simple and predetermines its applicability in different areas of activity, as well as for dispute resolutions by judicial inquiry and investigations.

The identification mark of remoteness of the event of its creation on a surface of a finished product or a fragment thereof according to the invention can be used in the claimed method for protecting a finished product or a fragment thereof against falsification of remoteness of event of its original creation for detecting such falsification by determining the remoteness of the event of application of such a mark on the finished product or the fragment thereof surface, coinciding with the date of application of a coating on the mark, and also for determining the remoteness of event of interference in the finished product or fragment thereof. It can find wide application in study of the remoteness of the event of man-made object, for example, articles of a high art value, unique articles, antiquarian articles, second-hand rare issuing, and other articles.

The claimed method for determination of the remoteness of an event of creation of a man-made object made of a cellulose-containing material in comparison with the known methods for determining the age of cellulose containing material or coatings on this material possesses the merits:
  sufficiently high accuracy of the results: accuracy to one month and in certain cases about several weeks;
  independence of the study results on artificial aging of an object;
  independence of the study results on the changes of properties of the coating applied on the object;
  the absence of significant damage of the object when taking samples: the samples are of a microscopic size;
  a possibility of accumulating statistical and experimental data for various technical expert examinations of man-made objects comprising fragments of a cellulose containing material with different types of coatings;
  a low threshold of determination of the remoteness of events of object creation—from 30 days;
  a possibility of determination of the remoteness of events of creation of art works by providing the antiques with firmly fixed identification marks indicating to any interference in them with a change of their form or composition of cellulose contained therein, by the state of the mark not corresponding to the remoteness of the event of application and not corresponding to cellulose parameters predicted for such dating, changing in time in a definite manner that allow one to find out falsifications of the remoteness of the creation event of the works of art.

The claimed method according to the invention for determination of the remoteness of an event of creation of a man-made object made of a cellulose-containing material can be performed using well known technological and measuring equipment, the identification mark creation on a man-made object surface can be made by means of well known processing methods from well known cellulose-containing materials plated with coatings made by means of known technologies and materials. The method according to the invention for protecting a finished product or a fragment thereof against falsification of remoteness of event of its original creation and method for determination of the remoteness of an event of creation of a man-made object made of a cellulose-containing material can be used in different spheres of activity of human beings.

The invention claimed is:

1. A method for determination of a remoteness of an event of creation of a man-made object being a finished product or a fragment thereof either having some external surface comprising a cellulose-containing material and at least a coating applied on the cellulose-containing material, the layer of coating being applied to form a coated area and to leave an uncoated area on an external surface of said finished product or a fragment thereof or having an identification mark of a remoteness of an event of its creation on a external surface of a finished product or a fragment thereof, the identification mark comprising: a cellulose-containing material, and at least a coating applied on the cellulose-containing material, the layer of coating being applied to form a coated area and to leave an uncoated area on an external surface of the mark, the method comprising:

providing a man-made object being said finished product or a fragment thereof;

taking cellulose-containing material surface layer samples from said coated and said uncoated areas;

measuring components and parameters of cellulose taken from cellulose-containing material surface layer samples on each area, including parameters of a free induction signal comprising (1) relaxation times $T_{2M}$ and $T_2$ of short and long components respectively of the free induction signal, (2) maximum amplitude $A_K$ and $A_D$ respectively of the short and long components of the free induction signal, and (3) a density of protons $Pr_1$, $Pr_2$ in the cellulose taken from the cellulose-containing material surface layer samples on the coated and uncoated areas, calculating $K_1$ and $K_2$, which are degrees of crystallinity of the cellulose from the uncoated and coated areas, according to a first common formula:

$$K=1-5(T_{2M}*A_D/T_2*A_K),$$

calculating values of $G_1$ and $G_2$, which are relative changes of cellulose parameters in each pair from uncoated and coated areas, at a time point $t_1$ of starting an analysis and at a time point $t_2$ after a predetermined time interval $\Delta t = t_2 - t_1$ according to a second common formula:

$$G=K_2/K_1+Pr_2/Pr_1, \text{ and}$$

carrying out a determination of a remoteness D of an event of a man-made object creation using a straight-line dependence function G(D) of relative changes G of the cellulose parameters in each pair from uncoated and coated areas on the remoteness D of the event of the coated area creation from a beginning at a time point of the remoteness D=0 when G=0 to an end at the time point $t_1$ of starting the analysis on a D-axis corresponding to each pair, when the relative changes $G_1$, $G_2$ were calculated for each pair from uncoated and coated areas at the time points $t_1$ and $t_2$, respectively, and the each function G(D) has an angle α of slope of the straight-line function G(D) to the D-axis value-based on tangent $\alpha=(G_2-G_1)/\Delta t$ and the value of D is calculated according to a third formula:

$$G(D)=[(G_2-G_1)/\Delta t] \cdot D,$$

where for $G_1$ at time point $t_1$, $D_1=G_1/[(G2-G1)/\Delta t]$, for a case when the value of the remoteness $D_1$ of the event of the coated area creation corresponding to each pair are the same, a conclusion made up of the remoteness D of the event of the man-made object creation is the same, and for a case when the value of the remoteness $D_1$ of the event of the coated area creation corresponding to each pair is different, the conclusion made up of the remoteness D of the event of the man-made object creation is related with a possibility of detecting any areas made by allowed or unwarranted interference in the man-made object surface after its initial preparation.

2. The method according to claim 1, wherein the components and parameters of the cellulose measured using nuclear magnetic resonance spectrometry.

3. The method according to claim 1, further comprising: taking the samples of the surface layer under a coating in the region of the highest density of the coating.

4. The method according to claim 1, wherein the samples have a minimum thickness of 0.05 mm and an area of not less than 0.3 mm².

5. The method according to claim 1 wherein the coating is made of a material selected from a group consisting of: colouring agents; varnishes; putties; fillings; art colours; typographical colours; colours stamp; pastes for ball pens; mastics for stamps; powders for cartridges of printing devices; ink for pens, capillary pens, gel pens, fountain pens and felt pens; indian ink; and biopolymeric ink for writing pens.

6. The method according to claim 1, wherein the man-made object is an identification mark of a remoteness of an event of its creation on the surface of a finished product or a fragment thereof, the identification mark comprising: a cellulose-containing material, and at least a coating applied on the cellulose-containing material when the cellulose-containing material is fixed onto the surface, the layer of coating being applied to form a coated area and to leave an uncoated area on an external surface of the mark, the mark is secured on the surface of a finished product or a fragment thereof by means of permanent connection which allows the cellulose-containing material samples to be taken from each of the areas without destruction of the mark, the method being used for determination of the remoteness D of the event of the man-made object creation according to the remoteness of the coated areas creation on a mark surface.

7. The method according to claim 1, wherein the man-made object is made of a material comprising the cellulose selected from a group consisting of: cotton, flax, wood of deciduous and/or coniferous breeds, helm, papyrus, bamboo, rice and wheaten straw.

8. The method according to claim 7, wherein the man-made object is made of a papier-mache.

9. The method according to claim 7, wherein the man-made object is made of wood or wood-shaving materials.

10. The method according to claim 7, the man-made object is made of a paper.

11. The method according to claim 10, wherein the man-made object is made of a paper selected from a group consisting of: offset paper, newspaper, advertisement paper, cream-laid paper, vellum paper, Chinese paper, coated paper, elephant paper, rice paper, tracing paper, pergament paper, Whatman paper, blotting paper, toilet paper, parchment paper, watermarked paper, and wall-paper.

12. The method according to claim 7, wherein the man-made object is made of cellulose-containing fibers.

13. The method according to claim 12, wherein the man-made object is made of woven or a knitted fabric selected from a group consisting of: a cottonous fabric, a cotton cloth, a rayon fabric, and a gobelin tapestry.

14. An identification mark of a remoteness of an event of its creation on a surface of a finished product or a fragment thereof, the identification mark comprising:

a cellulose-containing material; and at least a coating applied on the cellulose-containing material when the cellulose-containing material is fixed onto the surface, the layer of coating being applied to form a coated area and to leave an uncoated area on an external surface of the mark, wherein the mark is adapted for tight fixation onto the surface of a finished product or fragment thereof by means of permanent connection which provides for destruction of the mark at its unauthorized removal from the surface of the finished product or fragment thereof, wherein the mark is made to allow cellulose-containing material samples to be taken from a surface layer of surface areas of the mark for measurements of cellulose parameters, including parameters of a free induction signal and density of protons, on a surface of the uncoated area and under the coating of a surface of the coated area without destruction of the mark, wherein a remoteness of an event of creation of the identification mark on the surface of a finished product or fragment thereof is determinable by:

taking cellulose-containing material surface layer samples from coated and uncoated areas;

measuring components and parameters of cellulose taken from cellulose-containing material surface layer samples on each area, including parameters of a free induction signal comprising (1) relaxation times $T_{2M}$ and $T_2$ of short and long components respectively of the free induction signal, (2) maximum amplitude $A_K$ and $A_D$ respectively of the short and long components of the free induction signal, and (3) a density of protons $Pr_1$, $Pr_2$ in the cellulose taken from the cellulose-containing material surface layer samples on the coated and uncoated areas, calculating $K_1$ and $K_2$, which are degrees of crystallinity of the cellulose from the uncoated and coated areas, according to a first common formula:

$$K=1-5(T_{2M}*A_D/T_2*A_K),$$

calculating values of $G_1$ and $G_2$ which are relative changes of cellulose parameters in each pair from uncoated and coated areas, at a time point $t_1$ of starting an analysis and at a time point $t_2$ after a predetermined time interval $\Delta t = t_2 - t_1$ according to a second common formula:

$$G=K_2/K_1+Pr_2/Pr_1, \text{ and}$$

carrying out a determination of a remoteness D of an event of a mark creation using a straight-line dependence function G(D) of relative changes G of the cellulose parameters in each pair from uncoated and coated areas on the remoteness D of the event of the coated area creation from a beginning at a time point of the remoteness D=0 when G=0 to an end at the time point $t_1$ of starting the analysis on a D-axis corresponding to each pair, when the relative changes $G_1$, $G_2$ were calculated for each pair from uncoated and coated areas at the time points $t_1$ and $t_2$, respectively, and the each function G(D) has an angle $\alpha$ of slope of the straight-line function G(D) to the D-axis value-based on tangent $\alpha=(G_2-G_1)/\Delta t$ and the value of D is calculated according to a third formula:

$$G(D)=[(G_2-G_1)/\Delta t]\cdot D,$$

where for $G_1$ at time point $t_1 D_1 = G_1/[(G2-G2)/\Delta t]$, for a case when the value of the remoteness $D_1$ of the event of the coated area creation corresponding to each pair are the same, a conclusion made up of the remoteness D of the event of the mark creation is the same, and for a case when the value of the remoteness $D_1$ of the event of the coated area creation corresponding to each pair is different, the conclusion made up of the remoteness D of the event of the mark creation is related with a possibility of detecting any areas made by allowed or unwarranted interference in the mark surface after its initial preparation.

15. A method for protection of a finished product or a fragment thereof against falsification of a remoteness of an event of its original creation, the method comprising:

making the identification mark of claim 14; and fixing the identification mark on the surface of the finished product or the fragment thereof by means of permanent connection when the finished product or the fragment is prepared.

16. A method according to claim 14, wherein the finished product or fragment thereof is made of cellulose-containing material or of any another material.

17. The mark according to claim 14, wherein the cellulose-containing material is selected from a group consisting of: paper, fabric, and papier-mache.

18. A method for protection of a finished product or a fragment thereof against falsification of remoteness of an event of its original creation, the method comprising:

making the identification mark of claim 17; and fixing the identification mark on the surface of the finished product or the fragment thereof by means of permanent connection when the finished product or the fragment is prepared.

19. The mark according to claim 14, wherein the coating is made using a material selected from a group consisting of: colouring agents; varnishes; art colours; typographical colours; stamp colours; mastics; powders for cartridges of printing devices; indian ink; and biopolymeric ink for writing pens.

20. A method for protection of a finished product or a fragment thereof against falsification of remoteness of an event of its original creation, the method comprising:

making the identification mark of claim 19; and fixing the identification mark on the surface of the finished product or the fragment thereof by means of permanent connection when the finished product or the fragment is prepared.

21. The mark according to claim 14, wherein the mark is made to allow the cellulose-containing material samples to be taken that have a minimum thickness of 0.05 mm and an area of not less than 0.3 $mm^2$.

22. A method for protection of a finished product or a fragment thereof against falsification of a remoteness of an event of its original creation, the method comprising:

making the identification mark of claim 21; and fixing the identification mark on the surface of the finished product or the fragment thereof by means of permanent connection when the finished product or the fragment is prepared.

* * * * *